United States Patent [19]

Fellner

[11] Patent Number: 5,143,063
[45] Date of Patent: Sep. 1, 1992

[54] METHOD OF REMOVING ADIPOSE TISSUE FROM THE BODY

[76] Inventor: Donald G. Fellner, 40 E. 88th St., New York, N.Y. 10128

[21] Appl. No.: 153,963

[22] Filed: Feb. 9, 1988

[51] Int. Cl.$^5$ .............................................. A61F 7/00
[52] U.S. Cl. .................................. 128/399; 128/897; 128/783; 128/24.1; 600/2
[58] Field of Search ............... 128/804, 783, 897, 399, 128/653, 24 A, 24.1; 600/2, 10

[56] References Cited

U.S. PATENT DOCUMENTS

| | | | |
|---|---|---|---|
| 2,283,285 | 5/1939 | Pohlman | 128/804 |
| 3,028,857 | 1/1961 | Parker | 128/804 |
| 3,117,571 | 1/1964 | Fry et al. | 128/804 |
| 3,237,623 | 3/1966 | Gordon | 128/24 |
| 3,499,436 | 3/1970 | Balamuth | 128/804 |
| 3,499,437 | 3/1970 | Balamuth | 128/804 |
| 3,561,430 | 2/1971 | Filler, Jr. | 128/2.05 |
| 3,735,755 | 5/1973 | Eggleton et al. | 128/24 AA |
| 3,828,769 | 8/1974 | Mettler | 128/24 AA |
| 3,958,559 | 5/1976 | Glenn et al. | 128/2 V |
| 4,228,809 | 10/1980 | Paglione | 128/804 |
| 4,282,880 | 8/1981 | Gardineer et al. | 128/660 |
| 4,311,154 | 1/1982 | Sterzer et al. | 128/804 |
| 4,315,514 | 2/1982 | Drewes et al. | 128/653 |
| 4,324,250 | 4/1982 | Braun et al. | 128/395 |
| 4,343,301 | 8/1982 | Indech | 128/24 A |
| 4,374,516 | 2/1983 | Harrison | 128/804 |
| 4,381,009 | 4/1983 | Del Bon | 128/399 |
| 4,391,281 | 7/1983 | Green | 128/660 |
| 4,397,313 | 8/1983 | Vaguine | 128/399 |
| 4,397,314 | 8/1983 | Vaguine | 128/399 |
| 4,441,486 | 4/1984 | Pounds | 128/24 A |
| 4,527,550 | 7/1985 | Ruggera et al. | 128/1.5 |
| 4,586,512 | 5/1986 | Do-huu et al. | 128/660 |
| 4,597,379 | 7/1986 | Kihn et al. | 128/804 |
| 4,601,296 | 7/1986 | Yerushalmi | 128/804 |
| 4,622,972 | 11/1986 | Giebeler, Jr. | 128/399 |
| 4,638,436 | 1/1987 | Badger et al. | 128/401 |
| 4,646,756 | 3/1987 | Watmough et al. | 128/804 |
| 4,658,828 | 4/1987 | Dory | 128/660 |
| 4,658,836 | 4/1987 | Turner | 128/804 |
| 4,662,368 | 5/1987 | Hussein et al. | 128/398 |
| 4,674,481 | 6/1987 | Boddie et al | 128/804 |
| 4,718,429 | 1/1988 | Smidt | 128/400 |
| 4,757,820 | 7/1988 | Itoh | 128/24 A |
| 4,798,215 | 1/1989 | Turner | 128/804 |

FOREIGN PATENT DOCUMENTS 820814 9/1959 United Kingdom ............... 128/399

OTHER PUBLICATIONS

Bailey's Textbook of Microscopic Anatomy.
Douglas E. Kelly et al., Williams & Wilkins, 1984 p. 473.
Synopsis of Pathology, eighth ed., Anderson et al., Mosby Company, 1972 p. 333.
Harrison's Principles Of Internal Medicine, McGraw-Hill Book Company, Editors Petersdorf et al., 10th ed. 1983 pp. 570,571,1567.
Fritzsche, "With FDA Approval and Reimbursement in Place, Hyperthermia is Fourth Major Anticancer Weapon," *The Medical Business Journal*, Mar. 1986, pp. 80-82.
Yerushalmi et al., "Local Microwave Hyperthermia in the Treatment of Carcinoma of the Prostate," *Oncology*, vol. 43, pp. 299-305 (1986).
"Interim Report on Results of Treatments With the HTM-3000," HRI Inc.

*Primary Examiner*—Francis Jaworski
*Assistant Examiner*—George Manuel
*Attorney, Agent, or Firm*—Ostrolenk, Faber, Gerb & Soffen

[57] ABSTRACT

Electromedical apparatus is employed to non-invasively remove adipose tissue from the body by causing necrosis thereof by localizing (e.g., focusing) radiant energy. The radiant energy may be of any suitable kind, for example, localized radio frequency, microwave or ultrasound energy, which is impinged upon the cells to be eliminated. Cell destruction occurs through a mechanism such as, e.g., heating or mechanical disruption beyond a level which the adipose tissue can survive.

11 Claims, 2 Drawing Sheets

METHOD OF REMOVING ADIPOSE TISSUE FROM THE BODY

BACKGROUND OF THE INVENTION

1. Field of the Invention

This invention relates to electromedical methodology, and more specifically, to the employment of localized or focused radiant energy to remove adipose tissue by causing destruction or necrosis thereof.

2. Related Art

Adipose tissue, more commonly known as "fat", is formed of cells containing stored lipid. Fat cells are very large, ranging up to 120 microns in diameter. They are typically spherical but may assume polyhedral shapes because of mutual deformation. A single droplet of lipid occupies most of the volume of the cell. The nucleus is displaced to one side by the accumulated lipid and the cytoplasm is reduced to a thin rim comprising only about one fortieth of the total volume of the cell. Each cell is surrounded by delicate reticular fibers. In the angular spaces between the cells are capillaries that form a loose plexus throughout the tissue. Adipose tissue appears in section as a delicate network with large polygonal meshes.

Adipose tissue is often subdivided into small lobules by connective tissue septa. This compartmentation, visible with the naked eye, is most obvious in regions where the fat is subjected to pressure and has a cushioning or shock absorbing effect. In other regions, the connective tissue septa are thinner and the lobular organization of the tissue is less apparent.

Adipose tissue is widely distributed in the subcutaneous tissue but exhibits regional differences in amount, which are influenced by age and sex. In infants and young children there is a continuous subcutaneous layer of fat, the panniculus adiposus of rather uniform thickness over the whole body. In adults it thins out in some regions but persists and grows thicker in certain sites of predilection. These sites differ in the two sexes and are largely responsible for the characteristic differences in body form of males and females. In the male, the principal areas are the neck and the region overlying the seventh cervical vertebra, the subcutaneous area overlying the deltoid and triceps, the lumbrosacral region, and the buttocks. In the female, subcutaneous fat is most abundant in the anterior neck, the breasts, the buttocks, the epitrochanteric region, and the anterior aspect of the thigh. Few blood vessels pass through subcutaneous fat into the overlying skin, which receives its nutrients through a subdermal plexus of blood vessels which runs above the fatty layer.

In addition to these superficial fat deposits, there are extensive accumulations in both sexes in the omentum, mesenteries, and retroperitoneal areas. All of these areas readily give up their stored lipid during fasting. There are other areas of fat, however, that do not give up their stored fuel so readily. For example, the adipose tissue in the orbit, in the major joints, and on the palms of the hands and soles of the feet does not seem to be grist for the metabolic mill but instead has the mechanical function of support or protection. These areas diminish in size only after very prolonged starvation.

An excess of adipose tissue, i.e., obesity, may be unhealthful in that it gives rise to varying health problems in human beings both physical and psychological in nature. Beyond psychological effects such as poor self-image, obesity typically increases the risk of conditions such as heart disease, high blood pressure, osteoarthrosis, bronchitis, hypertension, diabetes, deep-vein thrombosis, pulmonary emboli, varicose veins, gallstones and hernias.

Thus, there is a clear need for improved methods of removing fatty tissue. Liposuction extracts adipose tissue from the body by purely mechanical means, but has undesirable side-effects due to the invasive nature of this process. To date, no non-invasive, and therefore reasonably safe, fatty tissue removal method has been developed.

Electromedical methods and apparatus have been used in the past for various surgical and therapeutic procedures. For example, U.S. Pat. No. 4,527,550 to Ruggera et al. discloses a radio frequency diathermy apparatus including means for localizing the heat focus U.S. Pat. No. 4,397,313 to Vaguine discloses a microwave hyperthermia apparatus including means for producing a concave electric field for focusing the electromagnetic energy at a particular region of the body. Federal Republic of Germany Patent 2,508,494 to Schulz, U.S. Pat. No. 4,343,301 to Indech, and U.S. Pat. No. 3,958,559 to Glenn et al. relate to ultrasound devices which can be focused on a tumor, for example, within the body.

However, these systems have not been used for fatty tissue removal. In fact, each of these systems recognizes the need to avoid damage to adipose or other tissue surrounding the tissue desired to be destroyed. See, e.g., U.S. Pat. No. 3,958,559 at col. 1, lines 24–25; U.S. Pat. No. 4,397,313 at col. 2, lines 45–57.

See also U.S. Pat. No. 4,601,296 to Yerushalmi, which notes at col. 1, lines 30–46 that known devices are capable of automatically controlling the undesired RF heating of healthy tissue. These devices monitor the temperature adjacent the work site, and responsively control the operation of the antenna and of a cooling system.

U.S. Pat. No. 4,397,314, to Vaguine, points out at col. 1, line 54–col. 2, line 11, that normal tissues are heated by prior art hyperthermia systems less effectively than tumors, since healthy tissue is characterized by a developed blood vessel network and a normal vasodilation response to heat, whereby blood flow may increase threefold after five minutes of heating, for example. On the other hand, tumors are characterized by a damaged blood vessel network and a blood flow that collapses during heating.

U.S. Pat. No. 4,441,486 to Pounds relates to ultrasound hyperthermia. This patent acknowledges the need to control the coverage of the hyperthermia treatment, but points out that with ultrasound this is not a great problem, since ultrasound does not preferentially heat fatty tissue.

According to Fritzsche, "With FDA Approval and Reimbursement in Place, Hyperthermia is Fourth Major Anticancer Weapon," The Medical Business Journal, March 1986, at 80–82, one capacitive RF hyperthermia device manufactured by Yamamoto in Japan is effective only where there is a low percentage of body fat.

The disclosures of the above-referenced patents and materials are incorporated by reference herein.

Thus, there is a recognition by the art that adipose tissue should not be heated inadvertently during hyperthermia, and a further recognition that adipose tissue, being more effectively blood-cooled than tumor tissue, is inherently unlikely to inadvertently receive a damaging energy dosage during hyperthermia treatment by means of the prior systems intended for treatment of tumors or the like.

OBJECTS AND SUMMARY OF THE INVENTION

Accordingly, a central object of the present invention is to provide electromedical methodology for non-invasively eliminating subcutaneous adipose tissue.

The above and other objects of the present invention are realized in an illustrative electromedical method which non-invasively causes necrosis of subcutaneous adipose ("fat") tissue by localizing (e.g., focusing) radiant energy. The radiant energy may be of any kind that can cause cell heating or physical disruption by being applied to the cells to be eliminated. For example, one of the above prior art systems may be employed to supply localized or focused radio frequency energy, microwave energy, or ultrasound energy, to the tissue to be destroyed.

Cell necrosis may be caused by local energy absorption which causes physical disruption, or elevates cell temperature to a level or for a period of time which the adipose structure cannot survive. Unfocused energy is not sufficient to cause injury to the overlying skin through which it passes harmlessly. Nor does using the energy to destroy the underlying fat cells injure the circulation to the skin, which is provided by the subdermal plexus, because the circulation provides a cooling effect.

BRIEF DESCRIPTION OF THE DRAWINGS

The above and other features and advantages of the invention will become more clear from the following detailed description of an illustrative embodiment thereof, presented hereinbelow in conjunction with the accompanying drawings, in which.

DETAILED DESCRIPTION OF AN ILLUSTRATIVE EMBODIMENT

Figure 1:
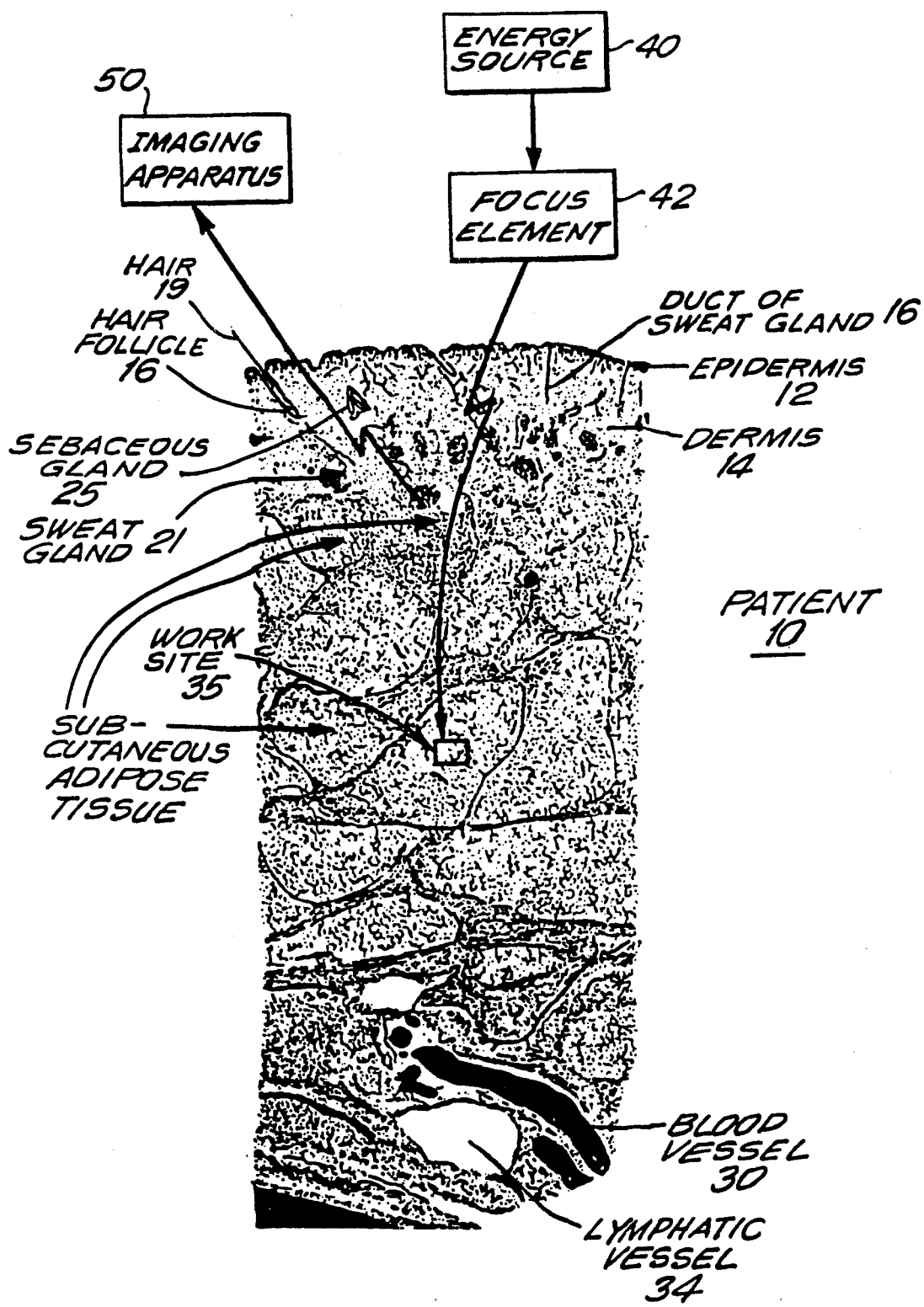
FIG. 1 is a schematic diagram depicting in cross-section the human epidermis, dermis and subcutaneous tissue, together with a block diagram of energy-applying and imaging apparatus in accordance with the principles of the present invention.

Referring now to FIG. 1, there is shown an illustrative system for removing subcutaneous adipose ("fat") tissue. In particular, the skin about a human subject 10 has an epidermis (outer) layer 12 disposed over a dermis layer 14. Passing through the epidermis 12 into the dermis 14 are sweat gland ducts 16 and hair follicles 16a through which hair 19 protrudes. Embedded in the dermis are sebaceous glands 25 and sweat glands 21. Immediately beneath the dermis is the subdermal plexus of small blood vessels (not shown for clarity). Disposed beneath the dermis is a layer, which is of varying thickness in different human beings, of subcutaneous adipose tissue 27. Beneath the fat layer are such structures as blood vessels 30 and lymphatic vessels 34.

As above noted, the subcutaneous adipose tissue layer 27 may be thin or within reasonable bounds in subjects of slight or moderate build. There are some people, however, in which the subcutaneous adipose tissue layer 27 becomes quite large; sometimes to the point of near disablement in cases of extreme obesity.

It is desirable to eliminate some (or some major part) of the subcutaneous adipose tissue for both cosmetic and fundamental health reasons as alluded to above. To this end, in accordance with the instant invention, an energy source 40 supplies radiant energy to a localizing (focusing) element 42. This focusing element 42 directs (focuses) the radiant energy to a particular zone of impingement in the subcutaneous adipose tissue layer 27 (e.g., at a work site 35 in FIG. 1). The energy source 40 may be of any kind per se well known to those skilled in the art which is capable of being localized by a focusing element 42, such that the emitted energy impinges at a variable, controlled focal location within the adipose layer 27. Thus, for example, the energy from the energy source 40 may comprise ultrasonic energy, radio frequency energy, microwave energy or the like.

One skilled in this art is aware that the heating of the work site 35 should be only to an effective temperature and for an effective duration, and should not exceed an amount of heating that will damage the surrounding tissue. The skilled person is also aware that no single specific combination of heating temperature and duration is appropriate for removal of adipose tissue in all subjects. Rather, these parameters appear to vary with the particular physiology of the individual subject, including such factors as body weight, health, age, sex and other factors.

Figure 2:
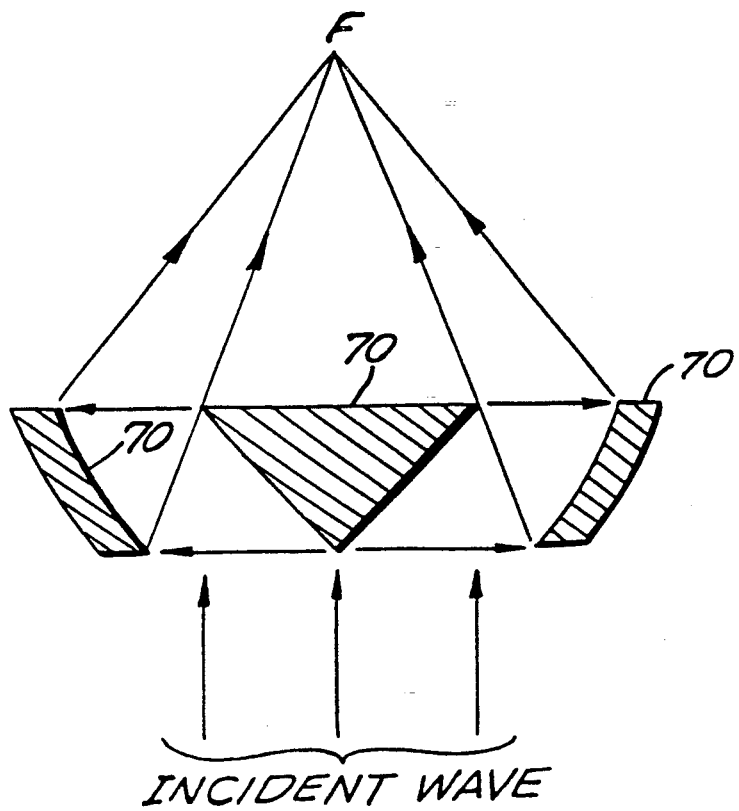
FIG. 2 is a cross-sectional view of a Barone reflector constituting one implementation of the focusing element 42 of FIG. 1.

The focus element 42 in the case of ultrasonic energy may comprise a lens having a flat planar surface on the radiation wave-incident side and a concave exit face as noted, for example, in a text entitled *Ultrasonics, Theory and Application* by G. L. Gooberman, Hart Publishing Co., New York (1959), at section 2.6. The use of such a focusing lens for ultrasound energy, with a planar wave-receiving face and concave wave-exiting face, is also described in an article "Deep Local Hyperthermia For Cancer Therapy: Extreme Electromagnetic And Ultrasound Techniques", A. Y. Cheung and A. Neyzari, *Cancer Research*, Vol. 44, October 1984, pp. 4736-4744. As is also per se well known, ultrasonic energy may be focused by a concave ceramic generator, or by employing a system of reflectors. An incident ultrasonic wave may be focused, for example, to a point F by a Barone reflector 70 as shown, for example, in FIG. 2.

Similarly, in the case of a radio frequency energy source 40, localizing (e.g., focusing) techniques and devices are per se well known to those skilled in the art. Most simply, radio frequency energy can be supplied by capacitive coupling directly to the skin for areas close to the dermis tissue via contact electrodes. Radio frequency induction focusing is per se well known to those skilled in the art, as by the use of plural focusing coils which are additive at the zone of interest and are elsewhere subtractive. Alternatively, the radio frequency energy may be focused by having a multiple beam phased array as is per se well known. For concave focusing see, for example, "Tumor Reduction By Radio Frequency Therapy Response In 21 Patients", H. H. LeVeen, et al., *JAMA*, Vol. 235 at 2198-2200. Alternative radio frequency focusing constructions are disclosed in "Equipment For Local Hyperthermia Therapy Of Cancer", C. F. Babbs, et al., *Medical Instrumentation*, Vol. 16, No. 5, September-October, 1982 at 245-248. The disclosures of each of the Gooberman, Cheung et al., LeVeen et al. and Babbs et al. texts identified above are hereby incorporated herein by reference.

In accordance with another aspect of the present invention, imaging apparatus 50 may be employed to view and monitor the adipose tissue necrosis process as it proceeds. The imaging apparatus may be of any kind per se well known to those skilled in the art, e.g., ultrasonic imaging, thermography or the like. These prior imaging systems permit quantitative measurement and calculation of fat cells destroyed and/or intended to be destroyed, for example, by complete automated area-/volumetric determination. Moreover, the localization (e.g., focus) of element 42 may be varied manually to progressively remove adipose cells. Alternatively, the focus of element 42 may be translated and refocused under automated control, e.g., by a stored-program control computer, or via controllers responsive to image presentation, to administer cell necrosis in a preprogrammed area of the patient. It may be desirable to destroy the fat cells a few at a time, employing multiple treatments to allow efficient removal of the waste products by the body.

EXAMPLE

Microwave energy, for example, may be focused on the work site 35 by employing an ellipsoid horn reflector wherein the energy source is at one focus of the antenna ellipse and the adipose tissue is at the other ellipse focus.

The incident energy supplied by the energy source 40 via the focusing element 42 is absorbed by cells at the work site 35. The absorbed energy increases the temperature of the adipose tissue located at the work site only, and should not substantially heat the surrounding tissue. The adipose tissue is heated to an effective temperature of at least about 110°-112° F. (43.3°-44.4° C.) and maintained at such temperature for at least about 30-40 minutes.

By maintaining the elevated temperature for an effective time, necrosis, i.e., localized cell death, occurs in the adipose cells. The extinguished cells are no longer part of the viable adipose tissue and the killed cells are removed from the body by the internal waste removal system of the body (as, for example, by the lymphatic system and/or phagocytes). By varying the focal point via the particular focusing element 42 employed, and monitoring the process by the imaging apparatus 50, adipose tissue is progressively removed beneath the dermis or within the adipose tissue layer as desired—both in position and in extent. Accordingly, the desired amount of unsightly and health-impairing fat is removed for the motivating cosmetic and/or health reason(s). Moreover, pursuant to current theory, and unlike tumor cells, for example, fat cells can only enlarge to cause obesity; they do not multiply. Thus, once a fat cell is destroyed, it is gone forever.

The above described arrangements are merely illustrative of the principles of the present invention. For example, as is per se well known, a bolus may be employed intermediate the focusing element 42 and the patient's epidermis 12 for more efficient communication of the impinging energy upon the subject. Other modifications and adaptations may occur to those skilled in the art, without departing from the spirit and scope of the present invention.

What is claimed is:

1. A method of controlling obesity in a human subject by non-invasively eliminating excess healthy adipose tissue from a subcutaneous adipose tissue layer of the human subject, comprising the steps of:

determining a desired work site in the subject's subcutaneous adipose tissue layer containing excess healthy adipose cells to be eliminated;

focusing radiant energy on said cells to raise the temperature thereof; and maintaining the energy focused on said work site until the excess healthy adipose tissue to be eliminated absorbs sufficient energy to cause cell destruction.

2. A method of claim 1, further comprising employing imaging apparatus for viewing said tissue destruction.

3. A method as in claim 1, further comprising employing imaging apparatus for determining the quantity of adipose tissue to be destroyed.

4. A method as in claim 1, wherein said energy is supplied from an ultrasonic energy source 5. A method as in claim 1, wherein said energy is supplied from a radio frequency energy 6. A method as in claim 1, wherein said energy is supplied from a microwave energy source.

7. A method as in claim 1, wherein the temperature at said work site is raised to substantially at least 43.3°-44.4° C.

8. A method as in claim 1, wherein said temperature at said work site is maintained for substantially at least 30-40 minutes.

9. A method as in claim 8, wherein the temperature at said work site is raised to substantially at least 43.3°-44.4° C.

10. A method as in claim 1, wherein said energy causes cell destruction by causing cell necrosis.

11. A method as in claim 1, wherein said work site is raised to a temperature sufficient to destroy adipose cells.

* * * * *